United States Patent
Waldman et al.

(10) Patent No.: US 6,460,014 B1
(45) Date of Patent: Oct. 1, 2002

(54) MODELING INTERACTIONS WITH ATOMIC PARAMETERS INCLUDING ANISOTROPIC DIPOLE POLARIZABILITY

(75) Inventors: Marvin Waldman; Carl Stephen Ewig; Jon Roger Maple, all of San Diego, CA (US)

(73) Assignee: Accelrys Inc., San Diego, CA (US)

( * ) Notice: Subject to any disclaimer, the term of this patent is extended or adjusted under 35 U.S.C. 154(b) by 0 days.

(21) Appl. No.: 09/148,810

(22) Filed: Sep. 4, 1998

Related U.S. Application Data

(60) Provisional application No. 60/057,945, filed on Sep. 5, 1997.

(51) Int. Cl.[7] ............................................. G06F 17/50
(52) U.S. Cl. ..................................... 703/5; 703/2; 703/7
(58) Field of Search ........................ 395/500.33, 500.32, 395/500.26, 500.27, FOR 364; 364/496; 703/2, 5, 7

(56) References Cited

U.S. PATENT DOCUMENTS

| | | | |
|---|---|---|---|
| 4,481,091 A | * 11/1984 | Brus et al. | 204/157.1 R |
| 4,939,666 A | * 7/1990 | Hardman | 364/496 |
| 5,025,388 A | 6/1991 | Cramer, III et al. | 364/496 |
| 5,420,805 A | 5/1995 | Still et al. | 364/578 |
| 5,448,498 A | * 9/1995 | Namiki et al. | 364/496 |
| 5,553,004 A | * 9/1996 | Grombech-Jensen et al. | 364/496 |
| 5,597,457 A | * 1/1997 | Craig et al. | 204/165 |
| 5,612,894 A | 3/1997 | Wertz | 364/496 |
| 5,612,895 A | 3/1997 | Balaji et al. | 364/496 |
| 5,705,335 A | 1/1998 | Hendry | 435/6 |
| 5,784,294 A | * 7/1998 | Platt et al. | 364/496 |
| 5,796,632 A | * 8/1998 | Kohtaro Yuta | 364/496 |

FOREIGN PATENT DOCUMENTS

| | | | |
|---|---|---|---|
| WO | WO 93/22737 | * | 11/1993 |
| WO | WO 97/19413 | * | 5/1997 |

OTHER PUBLICATIONS

Astrand, et al., "Molecular Dynamics study of water adopting a potential function with explicit atomic dipole moments and anisotropic polarizabilities." 1994.*

Uri Dinur, "Force Related Atomic Multipoles in Planar Molecules. Derivation of Atomic Quadrupole and Octupole Moments." 1990.*

Dinur, et al., "Determination of atomic point charges and point dipoles from the Cartesian derivatives of the molecular dipole moment and second moments, and from energy second derivatives of planar dimers. I. Theory." 1989.*

Dinur, U. and A. T. Hagler; J. Chem. Phys., vol. 91, No. 5, Sep. 1, 1989; Determination of atomic point charges and point dipoles from the Cartesian derivatives of the molecular dipole moment and second moments, and from energy second derivatives of planar dimers. *I. Theory*;; pp. 2949–2958.

(List continued on next page.)

Primary Examiner—Kevin J. Teska
Assistant Examiner—T. Phan
(74) Attorney, Agent, or Firm—Knobbe Martens Olson & Bear LLP

(57) ABSTRACT

Molecular modeling is performed using atomic parameters which include an anisotropic dipole polarizability tensor. Permanent atomic multipole parameters may also be included in the model. Energy evaluations including contributions from polarization energy and multipole interactions may be conducted which are useful in characterizing molecular properties for drug discovery, materials evaluation, and other applications.

22 Claims, 8 Drawing Sheets

OTHER PUBLICATIONS

Dinur, Uri; Journal of Computational Chemistry, vol. 12, No. 1, (1991); Force Related Atomic Multipoles in Planar Molecules. *Derivation of Atomic Quadrupole and Octupole Moments*; pp. 91–105.

Mayo, Stephen L., et al.; J. Phys. Chem., vol. 94, No. 26, (1990); *Dreiding: A Generic Force Field for Molecular Simulations*; pp. 8897–8909.

Anstrand, et al., Molecular Dynamics Study of Water Adopting a Potentional Function with Explicit Atomic Dipole Moments and Anisotropic Polarizabilities, (Feb. 1, 1995), Chemical Physics, vol. 191, No. 1–3, pp. 195–202.

* cited by examiner

MODELING INTERACTIONS WITH ATOMIC PARAMETERS INCLUDING ANISOTROPIC DIPOLE POLARIZABILITY

CROSS REFERENCE TO RELATED APPLICATIONS

This application claims priority under 35 U.S.C. §119(e) to U.S. Provisional Patent Application Ser. No. 60/057,945, entitled Molecular Models Incorporating Polarizability and Atomic Multipoles, filed on Sep. 5, 1997. The disclosure of the Molecular Models Incorporating Polarizability and Atomic Multipoles application is incorporated herein by reference in its entirety.

BACKGROUND

1. Field of the Invention

The invention relates to computation of interatomic and intermolecular interactions. Embodiments of the invention are applicable to chemical, physical, and biological research, and to the development of new pharmaceutical compounds.

2. Description of the Related Art

Over the last few years, significant advances have been made in predicting, studying, and quantifying the nature of interatomic and intermolecular interactions with the use of computer simulations. Although from a purely scientific point of view, such computer simulations can be useful in testing and validating a theory concerning the nature of these interactions, computer simulations find especially useful application in reducing the time required to develop new materials with desirable properties. Materials which may be developed with additional efficiency through the use of computer simulations include polymers, pesticides, herbicides, pharmaceuticals, semiconductor materials for integrated circuits, and petrochemicals to name a few.

Several modeling techniques are used in these environments. Typically, the model selected provides a user of the model with a particular compromise between physical accuracy and the computing resources required to run the model. Ab initio quantum mechanical calculations can be performed with a high degree of accuracy, but are very expensive in terms of the computer time required to perform them. In those fields described above, where new polymers, drugs, etc. are being developed, it is more useful to use modeling techniques which require less investment in computing resources, so that more candidate materials or molecules can be analyzed in a shorter time period for the properties desired.

Thus, it has become common to model interactions between groups of atoms, molecules, proteins, and other structures by defining an atom to atom potential which acts between the atoms of the system being analyzed. Generally speaking, the atom—atom potential defines the energy of the atomic system as that energy varies with the coordinates of the atoms. Intramolecular "bonded" interactions may include terms defining energy as a function of bond lengths, bond angles, torsion angles, and out-of plane coordinates. Intermolecular, or non-bonded potentials, typically include van der Waals interactions and electrostatic interactions. The benefit of these force field models is that the behavior of the atoms in the model is calculated using classical mechanics and electrostatics, which is significantly simpler computationally than performing the more mathematically complex quantum mechanical calculations.

However, because the systems being analyzed do not in fact behave classically, the models include parameters associated with the force field terms which are selected to fit known quantum mechanical molecular and atomic interactive behavior. In this way, a classically formulated force field is used to approximate quantum mechanical behavior at the atomic and molecular scale. A variety of force field models are known. Force field models are provided, for example, in U.S. Pat. No. 5,612,894 to Wertz, and in "DREIDING: A Generic Force Field for Molecular Simulations," *J. Phys. Chem.* 94, 8897–8909 (1990). An additional force field model, nicknamed "CFF", and which was developed by several of the inventors of the subject matter of the present application, is described in *J. Comp. Chem* 15, 162–182 (1994), and in *J. Am. Chem. Soc.* 116, 2515–2525 (1994). The disclosure of U.S. Pat. No. 5,612,894 and the Journal articles described above are hereby incorporated by reference in their entireties.

It can be appreciated that the selection of appropriate parameters and force field functional dependencies is a significant factor in the success of the model. Furthermore, the number of fitted parameters used in the model relative to the number of measurable or ab initio calculable values relevant to the system being modeled should be as low as possible. A model with as many fitted parameters as observables has little predictive value for systems which were not used in initially creating the fitted parameters.

Currently, most force fields treat interatomic electrostatic interactions using a partial charge model in which each atom is assigned a net charge and Coulomb's Law is used to calculate forces on each atom due to the other atoms of the system. The DRIEDING and CFF force fields mentioned above are examples. Another alternative which has been devised is to model a molecule as a set of bond centered dipoles. Neither treatment adequately models the interaction between atoms and the local electric fields. Accordingly, new force field parameterization schemes are needed to increase agreement with experiment, to maximize the number of observables relative to the number of parameters, and to limit the necessity of performing computationally expensive calculations.

SUMMARY OF THE INVENTION

The invention includes methods of evaluating a candidate molecule for suitability for a particular purpose. In one embodiment, the method includes selecting a candidate molecule and calculating a dipole moment induced in a first atom of the candidate molecule from a local electric field, wherein the induced dipole moment may be non-parallel to the local electric field. Using the calculated dipole moment, one or more physical properties of the candidate molecule may be predicted.

In another embodiment, a method according to the invention comprises parameterizing electrostatic behavior of the candidate molecule with a plurality of atomic parameters associated with at least one atom of the molecule, wherein the plurality of atomic parameters includes elements of an anisotropic atomic dipole polarizability tensor. The method also includes determining a dipole moment induced in the atom due to a local electric field using the atomic dipole polarizability tensor and predicting one or more physical properties of the candidate molecule using the induced dipole moment.

Embodiments of the invention also include apparatus for modeling the geometry and energy of interaction between first and second groups of atoms. The apparatus may comprise a memory storing an anisotropic atomic dipole polarizability tensor for at least one of the first group of atoms.

Also provided may be a processor for (1) modeling an electric field produced at least in part by the first and second groups of atoms, (2) retrieving the anisotropic dipole polarizability tensor, and (3) calculating a dipole moment induced in an atom of the first group by the electric field, and (4) calculating an interaction energy between the first and second groups of atoms which includes a contribution from the induced dipole moment. The apparatus may further include an output device for reporting the calculated interaction energy.

Another embodiment of the invention is a computer readable media having stored thereon commands which cause a general purpose computer to perform a method of modeling interactions between a first group of one or more atoms and a second group of one or more atoms. In one embodiment, the method comprises retrieving, for at least one of the first group of atoms, elements of an anisotropic atomic dipole polarizability tensor from a data storage device, modeling an electric field which is dependent on a relative orientation and separation of the first group of atoms and the second group of atoms. The method further includes calculating a dipole moment induced in the atom of the first group from the electric field using the anisotropic polarizability tensor, calculating an interaction energy between the first group of atoms and the second group of atoms which includes a contribution from the induced dipole moment, and outputting the interaction energy.

DETAILED DESCRIPTION OF THE INVENTION

Embodiments of the present invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention.

Figure 1:
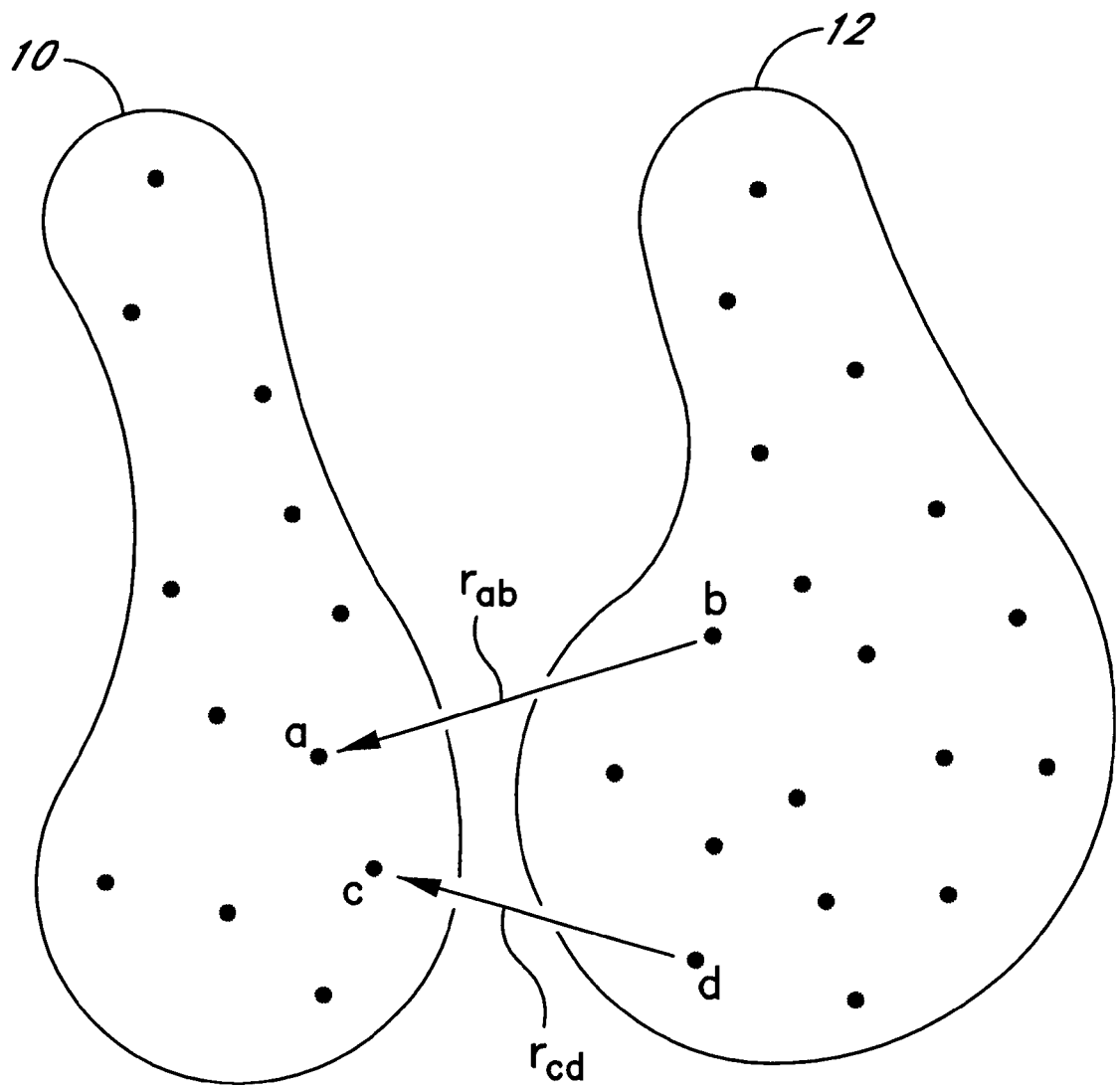
FIG. 1 is a perspective view of interacting atoms in a interaction model.

FIG. 1 is an illustration of a first group of atoms 10 and a second group of atoms 12 which are in a spatial relationship with one another. Atoms a and c of FIG. 1 are part of the first group 10 and atoms b and d are part of the second group 12. In some applications of the invention, each of the atoms in the first group 10 will be connected to at least one other atom of the first group 10 by a strong "bonded" interaction. Similarly, each of the atoms in the second group 12 will typically be connected to at least one other atom of the second group 10 by a strong bonded interaction. Interactions between atoms of the first group 10 and the second group 12 are typically of a "non-bonded" nature. Bonded interactions are characterized as strong, short range, and directional, while non-bonded interactions are generally characterized as weak, long range, and typically functions only of the distances $r_{ab}$ and $r_{cd}$ between non-bonded interacting pairs of atoms.

It will be appreciated, however, that the atom groupings need not necessarily be based on the bonded vs. non-bonded distinction, and that the forces on any given atom may result from a combination of bonded and non-bonded interactions with any of the other atoms in either of the atom groups. In some applications, the first group of atoms may comprise all of or a portion of a first molecule, and the second group of atoms may comprise all or a portion of a second molecule. Alternatively, the first and second groups of atoms may comprise different portions of the same molecule. In other applications of the invention, the second group of atoms comprises a reaction catalyst, and the first group of atoms is all or part of a substrate molecule. Interactions with surfaces, films, and crystal structures may also be defined as interactions between such first and second atom groups.

The location and types of atoms present in the first and second groups of atoms define a potential field which determines the energy of a given configuration of the system. The potential field may be expressed as a sum of terms, with each term representing a particular class of interaction. Most force fields include terms which represent bonded interactions, which are also sometimes referred to as intramolecular interactions. Terms relating to bonded interactions may include configuration energy shifts from bond stretching, angle bending, out of plane deformation, and possibly a variety of other molecular distortions from an unperturbed state. Any of the known parameterizations of the bonded interactions may be used with the present invention, and these intramolecular potential functions will not be described in further detail herein.

Non-bonded, or intermolecular interaction potentials generally include a van der Waals interaction and a parameterization of electrostatic interactions. The van der Waals term may take a variety of forms, and is attractive at large atomic separations and repulsive at small atomic separations. Different known parameterizations of the van der Waals term may be used with the present invention, and as with the intramolecular force parameters, will not be discussed in greater detail herein.

A general expression for a potential field used for molecular modeling may thus be described as follows:

$$\Phi = \text{Intramolecular terms} + \text{van der Waals terms} + \text{electrostatic terms} \quad (1)$$

The energy of a particular configuration of atoms is determined by summing the potential energy at points typically placed at atomic nuclear locations corresponding to the relevant atoms in the system being modeled. Forces acting on the atoms are determined by calculating the gradient of the potential energy field at the same atom centered points.

Turning now to the electrostatic terms of the potential energy field, some models restrict their consideration of electrostatic interactions to the assignment of a net charge to each atom. These net charges are used to compute a potential energy field at each atom centered point according to $q_i q_j / r_{ij}$ for each atom pair, where $q_i$ is the partial charge of atom i, $q_j$ is the partial charge of atom j, and $r_{ij}$ is the distance between atom i and atom j. The DREIDING and CFF force fields described above are examples of this type of field. It is one aspect of the invention that electrostatic interactions are treated in a more accurate manner. Specifically, each atom is assigned at least a dipole polarizability tensor which may be anisotropic. In some advantageous embodiments, each atom is modeled as a combination static charge, static dipole moment, static quadrupole moment, and a dipole polarizability which, as mentioned above, may be anisotropic for at least some of the atoms of the modeled system.

Figure 2:
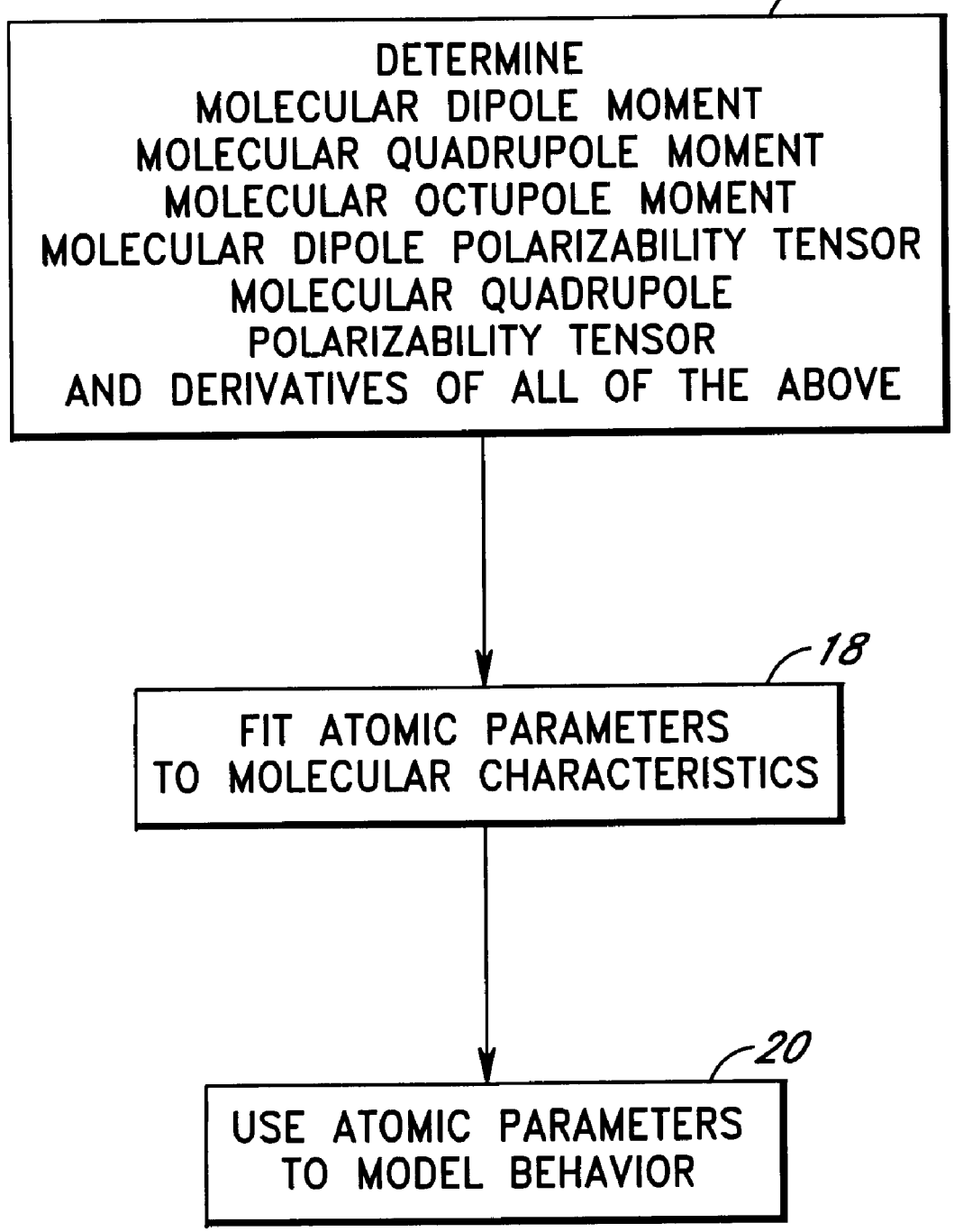
FIG. 2 is a flowchart illustrating the development and use of atomic parameters for modeling electrostatic interactions according to one embodiment of the invention.
Figure 3:
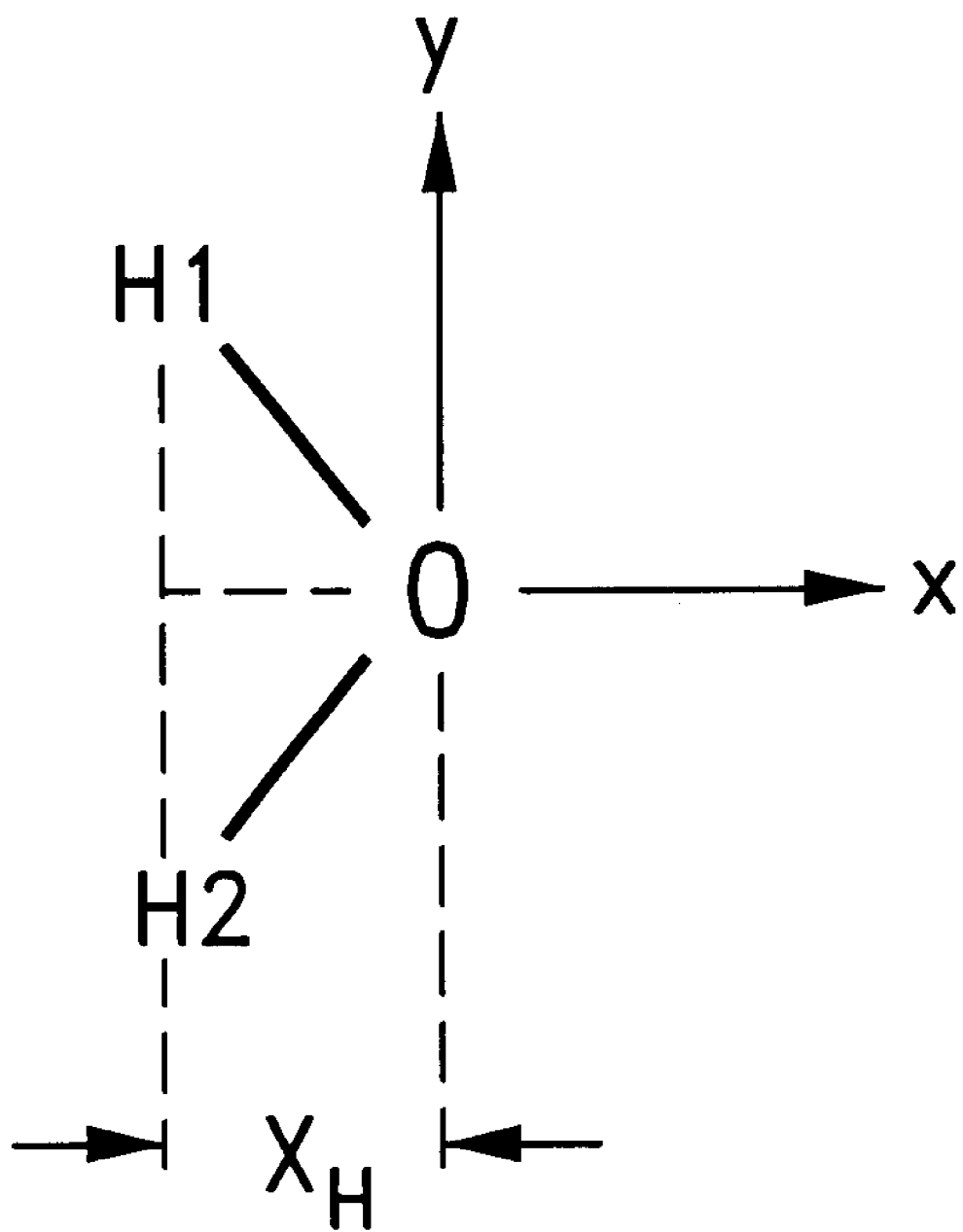
FIG. 3 is an illustration of a water molecule orientation which may be used in calculating a portion of an atomic parameter set.
Figure 4:
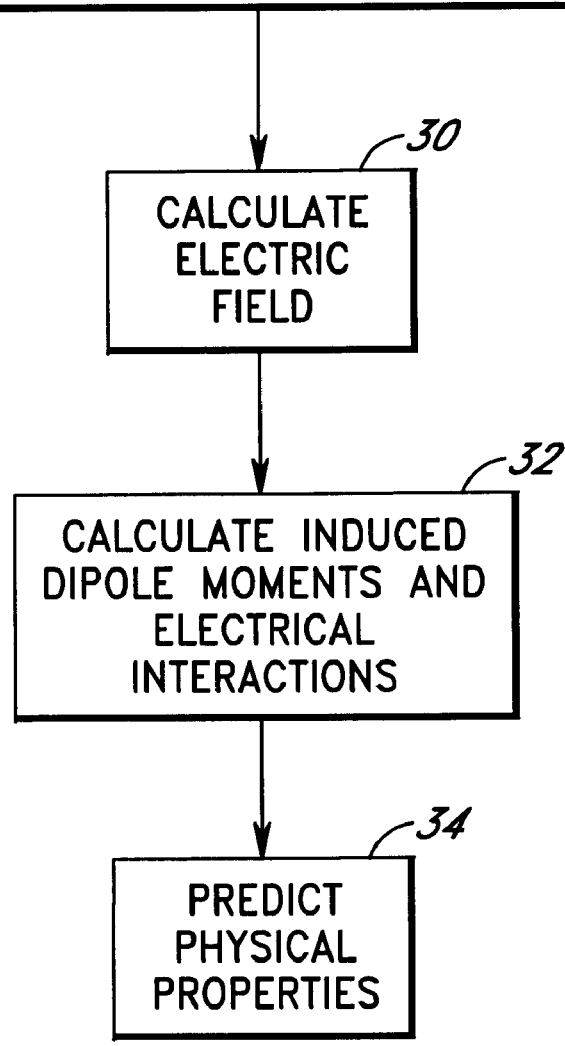
FIG. 4 is a flowchart of one method of implementing atomic parameterization according to the invention.

In FIGS. 2 through 4, parameterization of the electrostatic interactions according to one embodiment of the invention is set forth. As is explained more fully below, the values of the above mentioned parameters are selected by ensuring that the overall electrostatic properties of molecules or other aggregates of parameterized atoms reproduce accurate ab initio quantum mechanically calculated electrostatic properties of those molecules or aggregates. In other words, the potential field and polarization response produced by an atom centered arrangement of the chosen charge, dipole moment, quadrupole moment, and polarizability parameters will substantially match the potential field and polarization response produced by the actual molecules or other aggregates of atoms that the model is intended to simulate.

As will be appreciated by those in the art, the parameters associated with a given atom will be dependent on both the atom type and the other atoms it is bonded to. For example, an oxygen atom in an ether group will be parameterized differently than an oxygen atom in an aldehyde group. A large number of parameter sets may therefore be created which are devised to match those atomic aggregates which it is desired to model. If an interaction between a pair of molecules is to be modeled, as in an example set forth below, the atomic parameters are selected to reproduce molecular properties. Parameter derivations from selected functional groups rather than whole molecules may also be performed.

Referring now to FIG. 2, the creation of a parameter set for modeling the electrostatic interactions of a selected molecule begins at step 16. At this step, ab initio quantum mechanical calculations are used to compute values for a molecular dipole moment, molecular quadrupole moment, molecular octupole moment, molecular dipole polarizability tensor, molecular quadrupole polarizability tensor, and first derivatives with respect to atomic coordinates of all of these molecular quantities. Producing these values for molecular multipole moments, polarizabilities, and their derivatives is computationally expensive, and is performed only once in the initial parameter set production process.

At the next step 18, the desired atomic parameters are fitted to the previously determined molecular values. In one advantageous embodiment, the atomic parameters fitted to these quantum mechanical values include the atomic charges, dipoles, quadrupoles, and dipole polarizabilities discussed above.

One set of atomic parameters which may be calculated at step 18 is the partial charge assigned to each atom. The assignment of partial charges to atoms is a well established technique, and several methods of assignning charges to atoms in molecules or functional groups have been described. In one advantageous method, these values are arrived at by fitting the charge parameters (and the derivative of the charges with respect to internal coordinates, also called a charge flux) to the calculated molecular dipole moment. The mathematical relationship of molecular dipole moments (and their derivatives) to atomic charge parameters in planar molecules has been previously described, and one suitable method to select atomic charge parameters so as to fit an ab initio molecular dipole moment is described in detail by U. Dinur and A. T. Hagler in *J. Chem. Phys.* 91, 2949–2958 (1989). The disclosure of this *J. Chem. Phys.* article is incorporated herein by reference in its entirety.

Static atomic dipole moment parameters are also fitted to the molecular characteristics. Molecular models incorporating static atomic dipole moments have also been produced. In one advantageous model, the static atomic dipole moment parameters are mathematically related to the molecular quadrupole moment and its derivatives. For planar molecules, this relationship, and the derivation of atomic dipole parameters using it, is also described in the 1989 Dinur and Hagler article cited above. Step 18 may also comprise the calculation of static atomic quadrupoles. In one embodiment, these parameters may be fitted to the calculated molecular octupole moment and its derivatives. The construction of permanent atomic quadrupole parameters from molecular octupole moments and their derivatives is described in U. Dinur, *J. Comp. Chem.* 12, 91–105 (1991). The disclosure of this *J. Comp. Chem.* article is incorporated herein by reference in its entirety.

Additionally, step 18 may comprise a fit of atomic dipole polarizability tensor components to the molecular quadrupole polarizability tensor components and their derivatives. This procedure may be performed with manipulations which are described in additional detail below with reference to FIG. 3. Following the derivation of the desired atomic parameter set at step 18, the method of FIG. 2 moves to step 20 where interactions between groups of atoms are calculated using the atomic parameters in an atom—atom potential model.

With reference to the water molecule structure set forth in FIG. 3, the determination of atomic dipole polarizability tensor components from molecular quadrupole polarizability tensor components and their derivatives will now be described. As a starting point, use is made of the following expressions of the six unique elements of the molecular quadrupole moment in terms of atomic dipole moments and atomic partial charges:

$$\Theta_{xx} = \sum_i \left[ 2u_{ix}x_i - u_{iy}y_i - u_{iz}z_i + q_i\left(x_i^2 - \frac{1}{2}y_i^2 - \frac{1}{2}z_i^2\right)\right]$$

$$\Theta_{yy} = \sum_i \left[ 2u_{iy}y_i - u_{ix}x_i - u_{iz}z_i + q_i\left(y_i^2 - \frac{1}{2}x_i^2 - \frac{1}{2}z_i^2\right)\right]$$

$$\Theta_{zz} = \sum_i \left[ 2u_{iz}z_i - u_{ix}x_i - u_{iy}y_i + q_i\left(z_i^2 - \frac{1}{2}x_i^2 - \frac{1}{2}y_i^2\right)\right]$$

$$\Theta_{xy} = \frac{3}{2}\sum_i [u_{ix}y_i + u_{iy}x_i + q_i x_i y_i]$$

$$\Theta_{xz} = \frac{3}{2}\sum_i [u_{ix}z_i + u_{iz}x_i + q_i x_i z_i]$$

$$\Theta_{yz} = \frac{3}{2}\sum_i [u_{iy}z_i + u_{iz}y_i + q_i y_i z_i]$$

Where $\Theta_{ab}$ is the ab component of the molecular quadrupole moment, $u_{ia}$ is the a component of the dipole moment of atom i, $q_i$ is the partial charge of atom i, and $x_i$, $y_i$, and $z_i$, are displacements in the x, y, and z directions of atom i. From these equations, it is possible to express an induced molecular quadrupole moment in terms of induced atomic dipole moments as set forth below, if the explicit consideration of induced charges is ignored (i.e. $q_i'$ is set to 0):

$$\Theta'_{xx} = \sum_i [2u'_{ix}x_i - u'_{iy}y_i - u'_{iz}z_i]$$

$$\Theta'_{yy} = \sum_i [2u'_{iy}y_i - u'_{ix}x_i - u'_{iz}z_i]$$

$$\Theta'_{zz} = \sum_i [2u'_{iz}z_i - u'_{ix}x_i - u'_{iy}y_i]$$

$$\Theta'_{xy} = \frac{3}{2}\sum_i [u'_{ix}y_i + u'_{iy}x_i]$$

$$\Theta'_{xz} = \frac{3}{2}\sum_i [u'_{ix}z_i + u'_{iz}x_i]$$

$$\Theta'_{yz} = \frac{3}{2}\sum_i [u'_{iy}z_i + u'_{iz}y_i]$$

In the above equations, induced moments are indicated with a prime. By considering induced molecular quadrupole moments as sums of induced dipole moments caused by an external applied field, the molecular quadrupole polarizability tensor components can be related to components of atomic dipole polarizability tensors for the atoms in the molecule. For example, in an applied field in the x direction, $F_x$:

$$\Theta'_{zz} = \sum_i [2u'_{iz}z_i - u'_{ix}x_i - u'_{iy}y_i]$$

$$= F_x \sum_i [2\alpha_{i,xz}z_i - \alpha_{i,xx}x_i - \alpha_{i,xy}y_i]$$

$$= F_x A_{x,zz}, \text{ therefore}$$

$$A_{x,zz} = \sum_i [2\alpha_{i,xz}z_i - \alpha_{i,xx}x_i - \alpha_{i,xy}y_i]$$

Where $A_{a,bc}$ is the a, bc component of the molecular quadrupole polarizability tensor, and wherein $\alpha_{i,ab}$ is the ab component of the dipole polarizability tensor of atom i. Similar relationships may be derived in the same way by considering the other components of the induced quadrupole moment tensor and considering fields applied in the y and z directions. For example:

$$A_{x,xx} = \sum_i [2\alpha_{i,xx}x_i - \alpha_{i,xy}y_i - \alpha_{i,xz}z_i]$$

$$A_{x,xz} = \frac{3}{2}\sum_i [\alpha_{i,xx}z_i + \alpha_{i,xz}x_i]$$

$$A_{x,yz} = \frac{3}{2}\sum_i [\alpha_{i,xy}z_i + \alpha_{i,xz}y_i]$$

$$A_{z,xx} = \sum_i [2\alpha_{i,xz}x_i - \alpha_{i,yz}y_i - \alpha_{i,zz}z_i]$$

As these equations include sums over all the atoms in the molecule, there will be 6N unknowns, as there are six unique components of the dipole polarizability tensor for each of the N atoms in the molecule. Because there are only 18 unique and independent elements of the molecular quadrupole polarizability tensor, there may be many more unknowns than independent equations. For many molecules and functional groups, therefore, this set of equations will not lead to a unique determination of the complete set of atomic dipole polarizability parameters. For some classes of molecules, however, the additional consideration of the derivatives of the molecular quadrupole polarizability tensor components along with algebraic manipulation results in the simplification of the sums, and atomic dipole polarizability parameters may be uniquely calculated from the derivatives of the components of the molecular quadrupole polarizability tensor.

As an example, for a planar molecule in the x-y plane, the derivative of the molecular quadrupole polarizability tensor component $A_{z,xx}$ with respect to the z displacement of atom k is:

$$\frac{\partial A_{z,xx}}{\partial z_k} = -\alpha_{k,zz} + \sum_i \left[2x_i\frac{\partial \alpha_{i,xz}}{\partial z_k} - y_i\frac{\partial \alpha_{i,yz}}{\partial z_k}\right]$$

This derivative pulls $\alpha_{k,zz}$ (the zz component of the atomic dipole polarizability tensor for atom k) out of the sum over all the atoms. As another example, the derivative of the molecular quadrupole polarizability tensor component $A_{x,xz}$ with respect to the z displacement of atom k pulls $\alpha_{k,xx}$ (the xx component of the atomic dipole polarizability tensor for atom k) out of the sum over all the atoms as seen below:

$$\frac{\partial A_{x,xz}}{\partial z_k} = \frac{3}{2}\alpha_{k,xx} + \frac{3}{2}\sum_i x_i\frac{\partial \alpha_{i,xz}}{\partial z_k}$$

In some cases, these equations can be combined to cancel out the remaining sums over all atoms. For linear molecules located along the x-axis, where the y and z displacement of each atom may be set to zero after performing the derivatives, algebraic manipulation of the equations for the derivatives of the components of the molecular quadrupole polarizability tensor produces the following relationships:

$$\alpha_{k,xx} = \frac{1}{6}\left[4\frac{\partial A_{x,xz}}{\partial z_k} - 2\frac{\partial A_{y,yz}}{\partial z_k} - 3\frac{\partial A_{z,xx}}{\partial z_k}\right]$$

$$\alpha_{k,yy} = \alpha_{k,zz} = \frac{1}{6}\left[2\frac{\partial A_{y,yz}}{\partial z_k} - \frac{\partial A_{z,xx}}{\partial z_k} - 2\frac{\partial A_{z,yy}}{\partial z_k}\right]$$

For planar molecules, where only the z component of atomic displacement can be set to zero after performing the derivatives, the following relationships may be derived:

$$\alpha_{k,xx} + \alpha_{k,zz} = \frac{1}{3}\left[2\frac{\partial A_{x,xz}}{\partial z_k} - 2\frac{\partial A_{z,xx}}{\partial z_k} - \frac{\partial A_{z,yy}}{\partial z_k}\right]$$

$$\alpha_{k,xx} + \alpha_{k,yy} = \frac{1}{3}\left[2\frac{\partial A_{x,xz}}{\partial z_k} - 2\frac{\partial A_{y,yz}}{\partial z_k} - \frac{\partial A_{z,xx}}{\partial z_k} + \frac{\partial A_{z,yy}}{\partial z_k}\right]$$

$$\alpha_{k,xy} = \frac{1}{3}\left[\frac{\partial A_{x,yz}}{\partial z_k} + \frac{\partial A_{y,xz}}{\partial z_k} - \frac{\partial A_{z,xy}}{\partial z_k}\right]$$

From the above equations, it can be seen that for linear molecules, the components of the atomic dipole polarizability tensor for each atom can be computed arithmetically from the derivatives of the molecular quadrupole polarizability tensor components, which are calculated, as mentioned above, with high accuracy ab initio quantum mechanical calculations. For planar molecules, the off-diagonal elements of the atomic dipole polarizability tensor may be computed arithmetically, but only two equations exist for the three diagonal elements $\alpha_{k,xx}$, $\alpha_{k,yy}$, and $\alpha_{k,zz}$. For non-linear molecules therefore, the atomic dipole polarizability tensor components are not uniquely determined by the derivatives of the molecular quadrupole polarizability tensor components alone. Accordingly, calculations for non-linear molecules require simplifications and/or information derived from sources in addition to the molecular quadrupole polarizability tensor derivatives.

The computation of atomic dipole polarizability tensor components for the water molecule demonstrate this situation. In this case, coordinates can be selected such that the water molecule lies in the xy plane, with the oxygen atom at the origin as is illustrated in FIG. 3. In this configuration:

$$A_{z,xz} = \frac{3}{2}\sum_i [\alpha_{i,zz}x_i + \alpha_{i,xz}z_i]$$

$$= \frac{3}{2}\sum_i \alpha_{i,zz}x_i = 3\alpha_{H,zz}x_H$$

Thus, $\alpha_{H1, zz}=\alpha_{H2, zz}=A_{z,xz}/3x_H$. Using ab initio quantum mechanically computed values for $A_{z,xz}$ and $x_H$, a value for $\alpha_{H1, zz}$ and $\alpha_{H2, zz}$ of 0.0367 Å$^3$ results.

The value for $\alpha_{O,zz}$ may be determined by additional consideration of the zz component of the molecular dipole polarizability for the water molecule because $\alpha_{zz, water}=\alpha_{O, zz}+2\alpha_{H,zz}$. This leads to a value for $\alpha_{O,zz}$ of 0.361 Å$^3$.

The derivatives of the molecular quadrupole polarizability tensor of water may then be used according to the equations for planar molecules set forth above because the zz component of the tensor has been specified, resulting in unique values for the other dipole polarizability tensor components. When the quantum calculations of the molecular quadrupole polarizability tensor component derivatives are determined using HF/6-31G* quantum mechanical calculations, the atomic dipole polarizability tensor components for the atoms in a water molecule are (in units of Å$^3$):

$\alpha_{O,xx}=0.481$, $\alpha_{O,yy}=0.561$, $\alpha_{O,zz}=0.361$ $\alpha_{O,xy}=\alpha_{O,xz}=\alpha_{O,yz}=0$ $\alpha_{H1,xx}=\alpha_{H2,xx}=0.123$, $\alpha_{H1,yy}=\alpha_{H2,yy}=0.221$, $\alpha_{H1,zz}=\alpha_{H2,zz}=0.0367$ $\alpha_{H1,xy}=0.115$, $\alpha_{H2,xy}=-0.115$ $\alpha_{H1,yz}=\alpha_{H2,yz}=\alpha_{H1,xz}=\alpha_{H2,xz}=0$ As an isotropic dipole polarizability requires an equal value for all diagonal elements of the dipole polarizability tensor and zeros for all off diagonal elements, it may be noted that the atomic dipole polarizability tensors for the oxygen and both hydrogens in the water molecule are anisotropic. Both the oxygen and hydrogens are more polarizable in the y direction than they are in the x direction. Thus, for the water molecule as parameterized according to one embodiment of the invention, applied electric fields which are not exactly aligned with the x or y axis of the molecule will induce dipole moments which are not parallel to the applied field.

For molecules of N atoms in arbitrary three dimensional arrangements, the molecular quadrupole polarizability tensor components and their derivatives do not necessarily uniquely define the desired 6N atomic dipole polarizability tensor components. It will therefore be appreciated that the use of molecular symmetries and information in addition to the molecular quadrupole moment tensor and its derivatives may be used to develop atomic dipole polarizability tensors which fit molecular multipole quantities. In some cases, the atomic dipole polarizability tensor components can be formulated to fit the molecular dipole polarizability tensor and its derivatives in addition to the molecular quadrupole polarizability tensor and its derivatives. Furthermore, atomic parameters including the dipole polarizability tensor can be chosen to produce a simultaneous least squares fit to the multipole moments (and their derivatives) of a family of molecules, wherein each molecule of the family contains one or more atoms to be parameterized which are expected to behave similarly for each member of the family. It will also be appreciated that in many molecules and families of molecules; some of the terms in the equations above may be set to zero if their contribution is expected to be sufficiently small.

As illustrated in the flowchart of FIG. 2, the general molecular modeling scheme is to parameterize a complex quantum mechanical system with atom centered force field parameters, and then to use those parameters to model the behavior of the complex system. A general modeling method using the parameters described above is presented in FIG. 4. The first step 28 of the method comprises parameterizing the behavior of a selected system with one or more of the parameters mentioned above. These parameters may include a charge, a static atomic dipole, a static atomic quadrupole, and an anisotropic atomic dipole polarizability. It will be appreciated that not all of the atoms in a system need be parameterized with the above described parameter set. Furthermore, one or more atoms of the system may be parameterized with only a subset of these parameters, and one or more of the atoms of the system may be parameterized with additional parameters not specifically described herein.

In the next step 30, an electric field is calculated at the locations of one or more of the parameterized atoms of the system. This electric field may be due to the presence of the atoms, may be an applied field, or may be a combination of the two. In the presence of this electric field, induced dipole moments will be formed according to the atomic dipole polarizability parameters defined for the model. The assigned charges, static dipoles, induced dipoles, and static quadrupoles will also interact with the electric field local to each parameterized atom being considered. These effects are calculated at step 32. At step 34, one or more physical properties of the modeled system are predicted, based on the interactions calculated at step 32. It will be appreciated that a wide variety of physical properties may be determined in accordance with this embodiment of the invention. Optical properties, crystal structures, binding affinities, as well as other physical properties may be predicted. Calculated interaction energies may be used in several applications, including molecular dynamics simulations and Monte Carlo calculations where the interaction energy at a variety of molecular conformations and positions is used. In addition, energy minimizations may be performed to determine stable geometries of molecular interaction.

Figure 5:
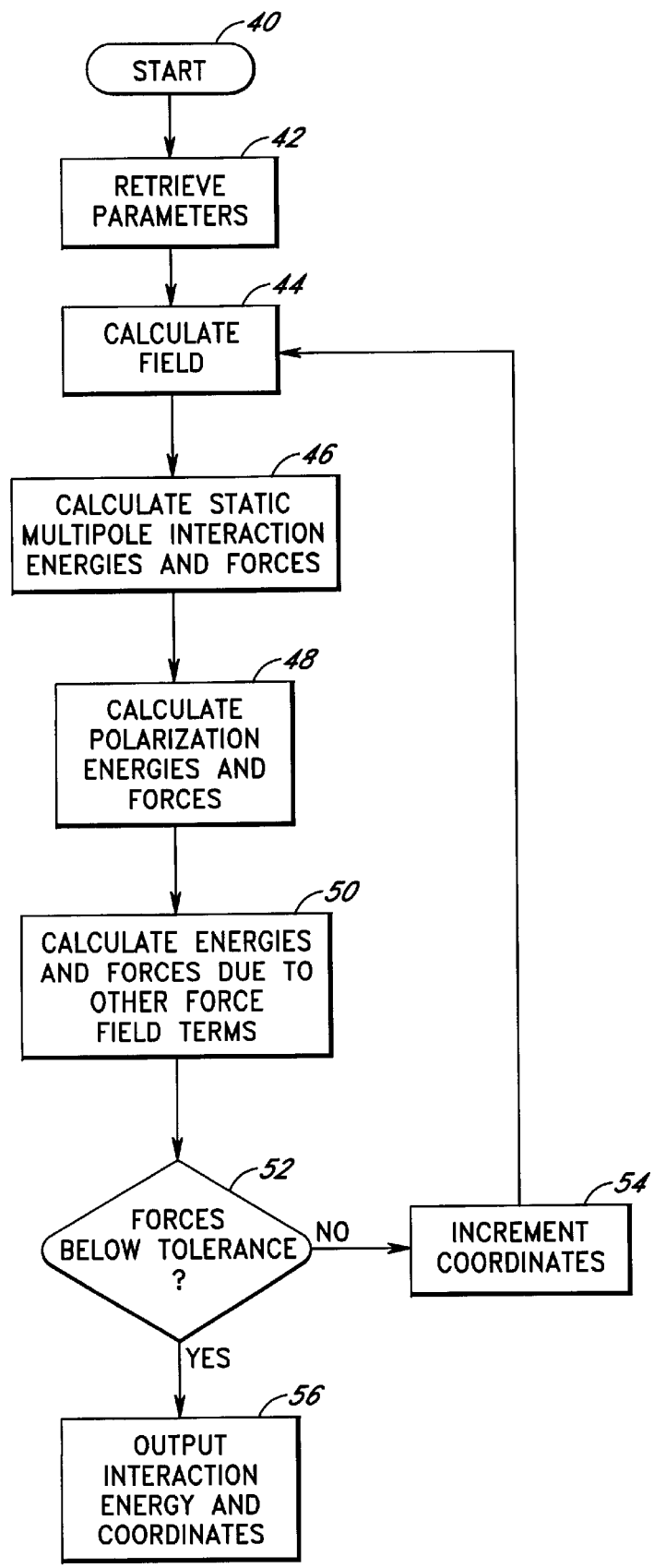
FIG. 5 is a flowchart of a geometry optimization method utilizing an embodiment of the invention.

In the field of pharmaceutical research, the geometry and energy of ligand binding is of significant interest. This application of the invention is illustrated in FIG. 5. Referring now to this Figure, one embodiment of a method for modeling geometries and energies of interaction between groups of atoms begins at a start state 40. It is assumed that the atom groups to be modeled are defined at this stage, and are placed in a starting configuration. In the pharmaceutical field, one group of atoms may comprise all or a portion of a selected candidate molecule such as a ligand molecule, and one group of atoms may comprise a portion of a protein. In this application, it may be of interest to determine the binding energy and geometry of the ligand-protein complex. Alternatively, two atom groups may comprise different portions of a protein, and the modeling may be performed to evaluate an intramolecular non-bonded interaction important in protein conformation. Following a prediction of physical properties using the modeling techniques herein described, candidate molecules may be synthesized and tested for the predicted physical properties.

It will be understood that in most applications, a general purpose computer is used to implement the methods described herein. The general purpose computer will have access to a data base of interaction parameters which is stored in a data storage device such as a CD-ROM, magnetic disk, semiconductor integrated circuit memory, or the like. The computer will also include a processor for accessing the data base, performing electric field calculations, computing induced dipole moments, calculating interaction energies, etc. Also included will be input and output devices for user interface such as keyboards, graphic display, printer, etc. The commands which configure such a general purpose computer to implement the methods of the invention are stored on a computer readable medium such as a CD-ROM for access by the general purpose computer.

Returning to a discussion of the method of FIG. 5, at step 42, force field parameters appropriate to the atoms and atomic bonds of the system being modeled are retrieved from the data base. These parameters will typically include parameters related to bonded interactions, van der Waals parameters, and electrostatic interaction parameters for atoms in a wide variety of molecules and functional groups. Which parameters are retrieved will of course depend on the atoms and functional groups of atoms being modeled.

At step 44, an electric field is calculated at the locations of the parameterized atoms. In this embodiment, this electric field may be calculated using classical electrostatics based on the pointwise arrangement of atomic charges, static and induced dipoles, and quadrupoles defined by (1) the parameters retrieved at step 42 and (2) the coordinates of the parameterized atoms of the system. Because the field depends on the induced dipoles, and the induced dipoles depend on the field, the field and induced dipoles are made self consistent using a procedure described in more detail with reference to FIG. 6.

Once the electric field is computed, at step 46 static multipole interaction energies and forces are determined. Classical electrostatics may be used to perform a pairwise computation of charge/charge, charge/static dipole, static dipole/static dipole, and charge/quadrupole interaction energies for the parameterized atoms of the system. At step 48, the polarization energy of the system is determined. The polarization energy is the contribution to the total energy which is attributable to the formation of induced dipoles according to the retrieved atomic dipole polarizability tensors.

According to this embodiment of the invention, therefore, the electrostatic and polarization contribution of the interaction energy between the atoms of the system which is calculated at steps 46 and 48 of FIG. 5 may be expressed as:

$$E = E_{q/q} + E_{q/u} + E_{q/u'} + E_{u/u} + E_{u/u'} + E_{u'/u'} + E_{q/Q} + E_{self}$$

wherein:

$$E_{q/q} = \text{charge / charge interaction energy} = \sum_{i>j} q_i q_j / r_{ij}$$

$$E_{q/u} = \text{charge / static dipole interaction energy} = -\sum_i u_i \cdot F_i^q$$

$$E_{q/u'} = \text{charge / induced dipole interaction energy} = -\sum_i u_i' \cdot F_i^q$$

$$E_{u/u} = \text{static dipole / static dipole interaction energy} = (-1/2)\sum_i u_i \cdot F_i^u$$

$$E_{u/u'} = \text{static dipole / induced dipole interaction energy} = \sum_i u_i \cdot F_i^{u'}$$

$$E_{u'/u'} = \text{induced dipole/induced dipole interaction energy} = -(1/2)\sum_i u_i' \cdot F_i^{u'}$$

$$E_{q/Q} = \text{charge / quadrupole interaction energy} = \sum_i q_i \Phi_i^Q$$

$$E_{self} = \text{self polarization energy} = (1/2)\sum_i u_i' \cdot \left(F_i^q + F_i^u + F_i^{u'}\right)$$

The total polarization energy contribution to the interaction energy is $E_{u/u'} + E_{u'/u'} \, E_{q/u'} + E_{self}$, which may be expressed as:

$$(-1/2)\sum_i \left[u_i \cdot F_i^{u'} + u_i' \cdot F_i^q\right]$$

Forces due to these interactions may be computed at steps 48 and 50 by perturbing the coordinates of the parameterized atoms and recalculating the interaction energies to determine the gradient of the interaction energy at the atomic coordinates. One process for determining the polarization energy gradient (and thus the polarization forces) is explained in more detail with reference to FIG. 7. At step 50, interaction energies and forces are computed for force field terms not described with reference to steps 46 and 48, including the intramolecular and van der Waals energies and forces.

If the current atomic configuration is a stable configuration of the system, the calculations performed at steps 46, 48, and 50 above will result in calculated forces on the atoms of near zero. At step 52, therefore, it is determined whether or not these forces are below a threshold value. If they are not, at step 54, the coordinates of the atoms of the system are incremented. In one embodiment, the incrementing is done in the direction of the energy gradient, although other energy minimization algorithms could be used with similar results. After the coordinates are incremented, the method loops back to step 44 to recalculate the field with the atoms at their new coordinates. An iterative energy minimization process may therefore be performed until the forces on the atoms of the system are below the threshold at step 52. This indicates that a stable geometry has been reached, and at step 56 a computed total interaction energy and the stable atomic coordinates are output.

Figure 6:
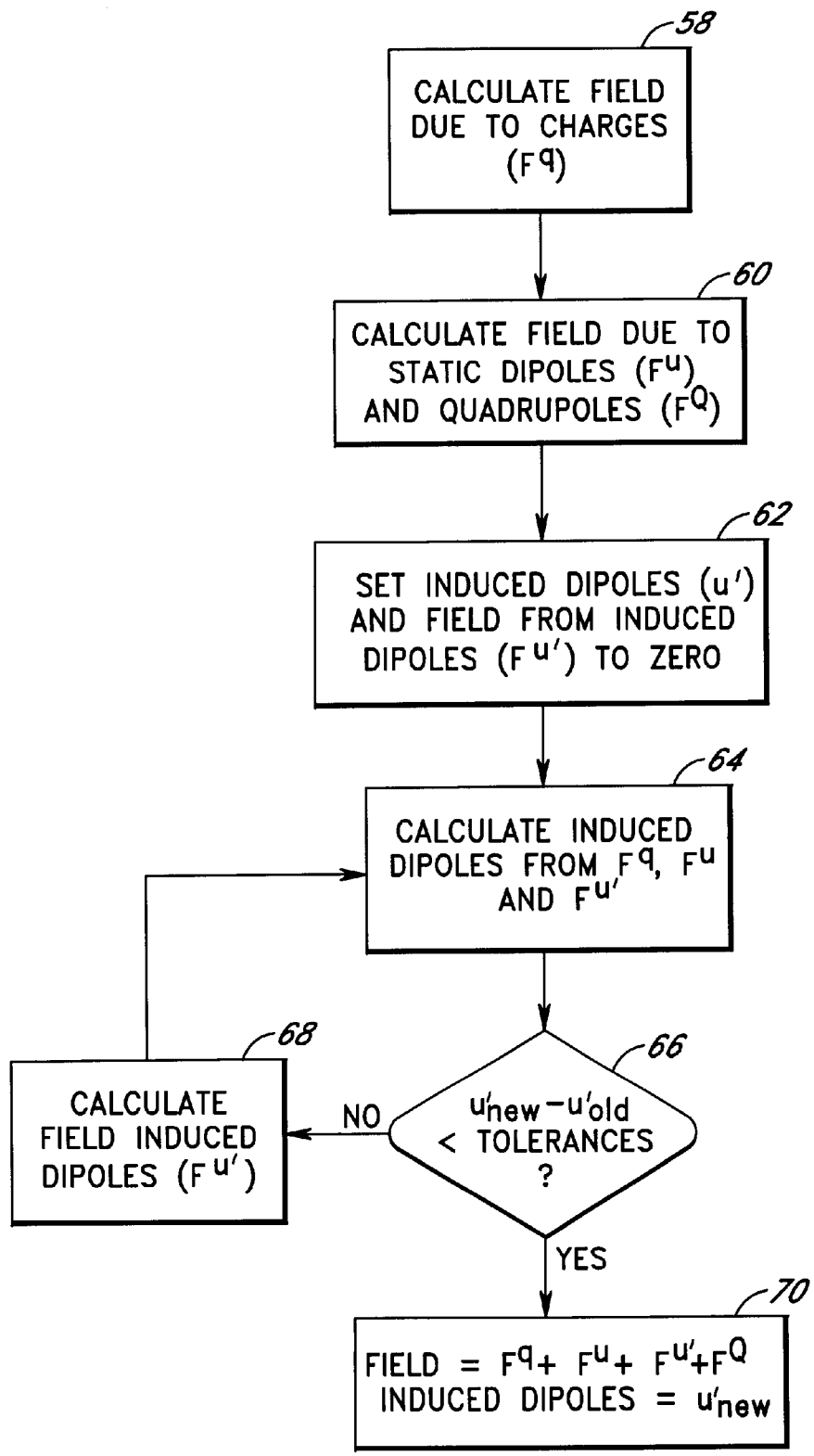
FIG. 6 is a flowchart of one method of calculating polarization energies in the geometry optimization method of FIG. 5.

FIG. 6 is a flowchart illustrating an iterative method of making the local electric fields and the induced dipoles self consistent when the field is calculated at step 44 of FIG. 5.

The method begins at step 58, where the field due to the static charges assigned to each atom is determined at each atomic location. Next, at step 60, the field at each atomic location from the static dipoles and quadrupoles of each parameterized atom is calculated. Initially, at step 62, the induced atomic dipoles and the field produced by induced atomic dipoles for each atom are set to zero. At step 64, the induced dipoles formed by the presence of the current calculated field are determined using the anisotropic atomic dipole polarizability tensors discussed at length above. In the first iteration of the method of FIG. 6, the field will be due solely to the contributions from the static multipoles calculated at steps 58 and 60, as the induced dipoles and the field resulting from them are initially zero.

Next, at decision state 66, the new induced dipoles for each atom are compared to the old induced dipoles. If the difference for any of the parameterized atoms is greater than a threshold value, the dipoles and field are not considered self consistent. In this case, the field due to the induced dipoles is calculated at step 68, and the method loops back to step 64, where a new set of induced dipoles are determined. This new set of induced dipoles are computed with reference to the local fields as updated with the contribution from the induced dipoles calculated in the last iteration.

This iterative loop continues until the new induced dipoles are sufficiently close to the last induced dipoles at step 66, which indicates self consistency between the electric field and the atomic dipole moments induced by the electric field. Once this point is reached, the field and induced dipoles are set to the values produced by the last field-induced dipole update iteration at step 70. Although an iterative method is illustrated in FIG. 6, those in the art will recognize that an analytical matrix inversion method could also be used to accomplish the same result.

Figure 7:
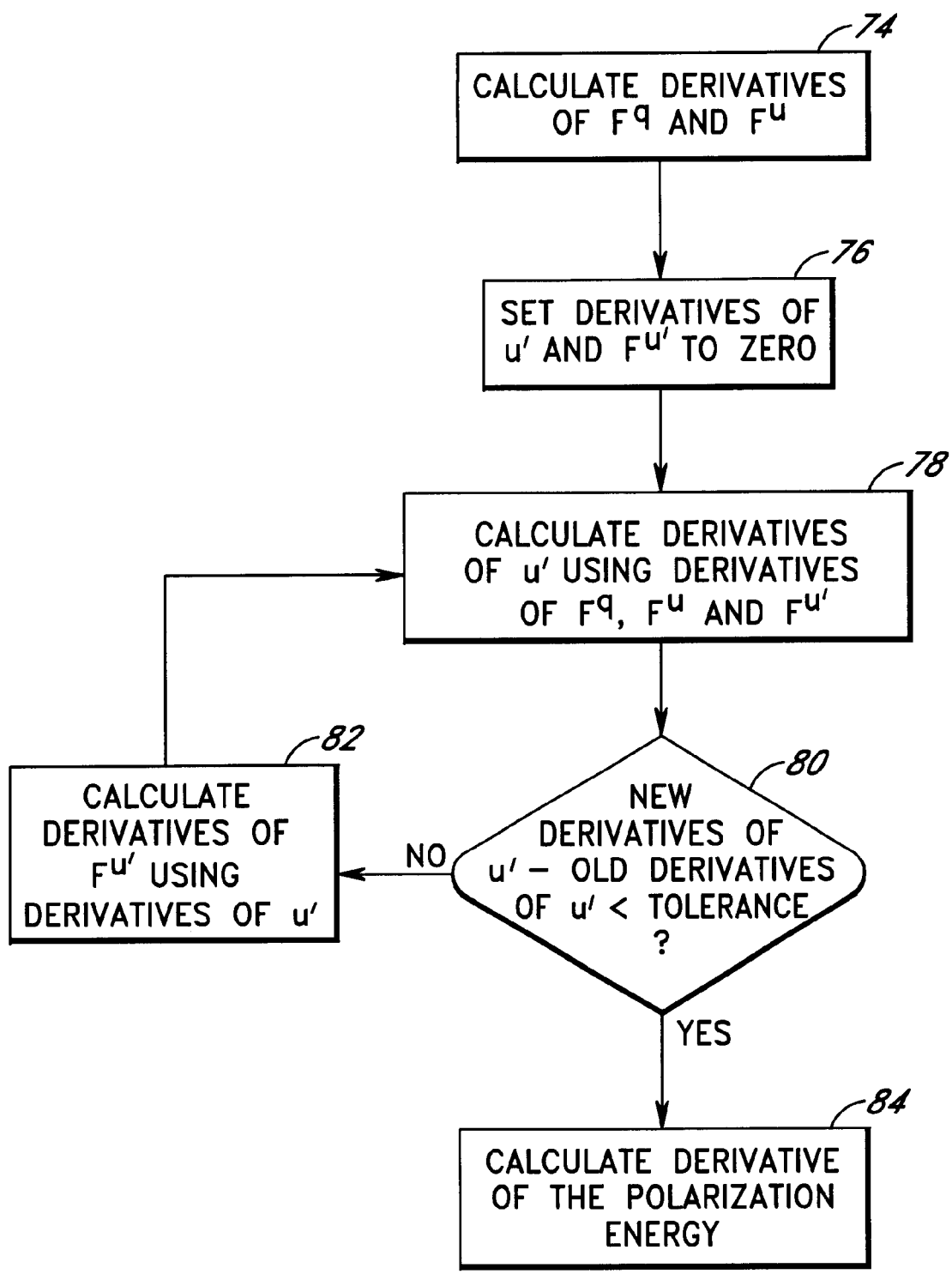
FIG. 7 is a flowchart of one method of calculating polarization forces in the geometry optimization method of FIG. 5.

FIG. 7 illustrates an iterative method for calculating the polarization forces at step 48 of FIG. 5. Referring back to the formula for the polarization energy given above, it can be seen that the gradient of the polarization energy may be written as:

$$\frac{\partial E_{pol}}{\partial x_j} = (-1/2) \sum_i u_i \cdot \frac{\partial F_i^{u'}}{\partial x_j} + u_i' \cdot \frac{\partial F_i^q}{\partial x_j} + \frac{\partial u_i'}{\partial x_j} \cdot F_i^q + \frac{\partial u_i}{\partial x_j} \cdot F_i^{u'}$$

Thus, a calculation of the polarization energy gradient requires the determination of the derivatives of the induced dipoles themselves, the derivatives of the field due to the induced dipoles, and the derivatives of the field due to the atomic charges. To determine the derivatives of the induced dipoles, it is additionally required to determine the derivatives of the field due to the static atomic dipoles. In an iterative manner analogous to that illustrated in FIG. 6, the derivatives of the field due to the induced dipoles is made self consistent with the derivatives of the induced dipoles themselves. This method begins at step 74 of FIG. 7 where the derivatives of the field due to the atomic charges and the field due to static dipoles are determined. Next, at step 76, the derivatives of the induced dipoles and the field due to the induced dipoles is set to zero. At step 78, the derivatives of the induced dipoles are then calculated. In the first iteration, this derivative is calculated using only the derivatives of the fields due to the charges and the static dipoles, as the derivatives of the induced dipoles is set to zero.

The method next moves to a decision state 80, where the new values of the derivatives of the induced dipole moments are compared to the prior derivatives of the induced dipole moments for each parameterized atom. If the result of these comparisons is more than a given threshold, the induced dipole derivatives are not consistent with the induced dipole field derivatives. In this case, the method moves to step 82 and new derivatives of the induced dipole field are calculated using the derivatives of the induced dipoles calculated in the last iteration at step 78. From step 82, the method loops back to step 78, and recalculates new derivatives of the induced dipole moments using the derivatives of the induced dipole field derivatives calculated in step 82.

If at step 80 it is determined that the differences between the newly calculated derivatives of the induced dipole moments and the prior derivatives of the induced dipole moments from the last iteration are less than a threshold value, the induced dipole derivatives are considered consistent with the induced dipole field derivatives. In this instance, the method moves to step 84, where the polarization energy gradient is determined using the final values for the induced dipole derivatives and induced dipole field derivatives.

Figure 8:
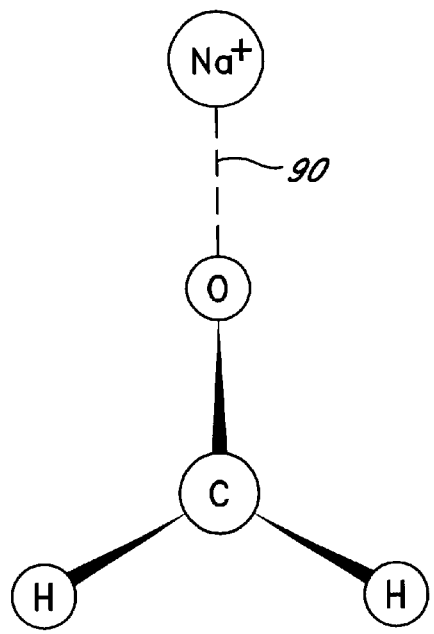
FIG. 8 is a perspective view of an optimized $Na^+$-formaldehyde complex.
Figure 9:
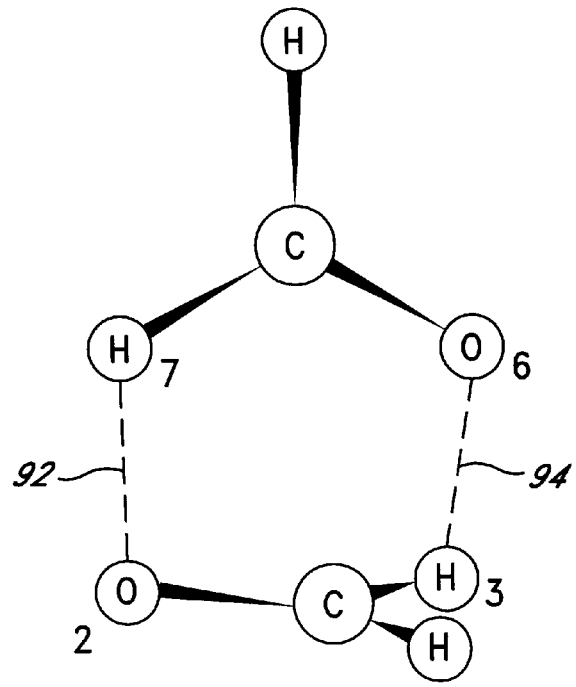
FIG. 9 is a perspective view of an optimized formaldehyde dimer.

With reference now to FIGS. 8 and 9, examples of interaction energies and geometries calculated using a force field including static atomic multipoles and anisotropic atomic dipole polarizabilities are presented. In the first example, illustrated in FIG. 8, the structure and interaction energy of the formaldehyde/sodium ion complex was modeled. The force field used in this model included charge, static dipole, and static quadrupole parameters, as well as atomic dipole polarizability tensor components as described above. The van der Waals parameters were adjusted such that the optimized $Na^+$/O distance 90 equaled 2.16 Å, which is the value calculated using ab initio quantum mechanical methods.

The interaction energies determined by the model (in kcal/mole) are:
intramolecular: 0.02
van der Waals: 7.88
charge/charge: −25.40
charge/static dipole: −2.61
charge/static quadrupole: 2.77
polarization: −12.29
TOTAL: −29.63

These values may be compared to a quantum mechanically calculated total interaction energy of −28.3 kcal/mole (generated using HF/6-31G* with a basis set superposition error correction). In contrast, using a force field model which includes only charge/charge electrostatic interaction parameterization, the polarization energy is neglected, and a value of approximately −18 kcal/mole is obtained. The inclusion of atomic dipole polarizabilities in the model parameter set thus greatly improves the match between the predictions of the force field calculations and the computationally expensive quantum mechanical calculations.

Referring now to FIG. 9, an optimized structure of the formaldehyde dimer is illustrated. Using quantum mechanical calculations (MP2/6-31+G(2df, 2pd)), the predicted optimized structure comprises a perpendicular stacked structure, with the distance between atoms O2 and H7 (denoted 92 in FIG. 9) being 2.38 Å, and the distance between atoms O6 and H3 (denoted 94 in FIG. 9) being 2.81 Å. The quantum mechanically calculated interaction energy is −4.6 kcal/mole.

Using a force field including charge, static dipole, static quadrupole parameters, and atomic dipole polarizability tensor components, the optimized structure produced by the model is the perpendicular stacked structure wherein the distance between atoms O2 and H7 92 is 2.77 Å, and the distance between atoms O6 and H3 94 is 3.05 Å. The calculated interaction energy using this parameterized model is −4.5 kcal/mole.

If the parameterized model includes only charge/charge electrostatic interaction terms, the wrong optimized structure is predicted. The upper formaldehyde molecule lies flat on top of the lower formaldehyde molecule, and the O2-H7 and O6-H3 distances are both equal to 3.17 Å. By running the formaldehyde dimer optimization with different models which consider only subsets of the charge/charge, charge/static dipole, static dipole/static dipole, charge/quadrupole, and polarization interactions, it has been found that the charge/quadrupole interaction appears significant in the formation of the optimized perpendicular stacked structure rather than the flat stacked structure.

Molecular models in accordance with the invention therefore provide increased accuracy in predicting the physical properties of subject molecular systems. This will be especially true in those systems which include significant anisotropic polarizations, such as systems including ion-benzene interactions. Because the parameter set is created to fit higher order molecular moments and polarizabilities, more accurate energy calculations should result, as these molecular properties often contribute significantly to interaction energies, and are not adequately taken into account in current modeling schemes. Furthermore, the ratio of parameters to quantum observables can be increased by fitting, for an N atom molecule, 6N atomic dipole polarizability parameters to 18 molecular quadrupole polarizability tensor components and 54N derivatives of those components.

The foregoing description details certain specific embodiments of the invention: It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended Claims and any equivalents thereof.

What is claimed is:

1. A computer implemented method of modeling an interaction between a first group of one or more atoms and a second group of one or more atoms, wherein at least a portion of said first group of one or more atoms is characterized by a quadrupole polarizability tensor, said method comprising:

defining, for at least a first atom of said first group of atoms, elements of an atomic dipole polarizability tensor utilizing derivatives of elements of said quadrupole polarizability tensor;

calculating a dipole moment induced in said at least a first atom of said first group of atoms by a local electric field, said local electric field being dependent on a relative orientation and separation of said first group of one or more atoms and said second group of one or more atoms;

determining an interaction energy between said first group of one or more atoms and said second group of one or more atoms which includes a contribution from said induced dipole moment; and outputting said interaction energy.

2. The method of claim 1, wherein said first group of one or more atoms comprises a first molecule, and said second group of one or more atoms comprises a second molecule.

3. The method of claim 1, wherein said first group of one or more atoms comprises a first portion of a molecule, and wherein said second group of one or more atoms comprises a second portion of said molecule.

4. The method of claim 1, wherein said second group of one or more atoms comprises a catalyst.

5. The method of claim 1, wherein said atomic dipole polarizability is anisotropic.

6. The method of claim 5, wherein said electric field and said induced dipole moment are not parallel.

7. The method of claim 1, wherein said first molecule is also characterized by a molecular quadrupole moment tensor, and wherein said method additionally comprises defining elements of an atomic dipole moment tensor for said first atom utilizing derivatives of said molecular quadrupole moment tensor.

8. The method of claim 1, wherein said first molecule is also characterized by a molecular octupole moment tensor, and wherein said method additionally comprises defining elements of an atomic quadrupole moment tensor for said first atom utilizing derivatives of said molecular octupole moment tensor.

9. The method of claim 8, wherein said calculated interaction energy additionally comprises a contribution from said atomic quadrupole.

10. A method of evaluating a candidate molecule for suitability for a particular purpose, said candidate molecule comprising a plurality of bonded atoms, said method comprising:

parameterizing behavior of said candidate molecule with a plurality of atomic parameters associated with at least one of said plurality of bonded atoms, said plurality of atomic parameters including elements of an anisotropic atomic dipole polarizability tensor which was derived from elements of a quadrupole polarizability tensor of said candidate molecule;

determining a dipole moment induced in said at least one of said plurality of atoms due to a local electric field using said atomic dipole polarizability tensor; and predicting one or more physical properties of said candidate molecule using said induced dipole moment.

11. The method of claim 10, additionally comprising:

synthesizing said candidate molecule; and testing said synthesized candidate molecule for said one or more physical properties.

12. The method of claim 10, wherein predicting one or more physical properties of said candidate molecule comprises calculating a polarization energy.

13. The method of claim 10, wherein predicting one or more physical properties of said candidate molecule comprises determining an energy of interaction between said candidate molecule and a target molecule.

14. The method of claim 10, wherein said plurality of parameters additionally includes a permanent atomic quadrupole moment.

15. The method of claim 14, wherein said plurality of parameters additionally includes a permanent atomic dipole moment.

16. The method of claim 15, wherein said plurality of parameters additionally includes an atomic charge.

17. The method of claim 16, additionally comprising calculating an energy of interaction between said local electric field and said permanent atomic quadrupole moment, permanent atomic dipole moment, and atomic charge, and wherein predicting one or more physical properties of said candidate molecule comprises using said energy of interaction between said candidate molecule and said target molecule.

18. A computer readable medium having stored thereon commands which cause a general purpose computer to perform a method of modeling interactions between a first group of one or more atoms and a second group of one or more atoms, said method comprising:

retrieving, for at least one of said first group of atoms, elements of an anisotropic atomic dipole polarizability tensor which was derived from elements of a quadrupole polarizability tensor of said first group of one or more atoms from a data storage device;

modeling an electric field which is dependent on a relative orientation and separation of said first group of atoms and said second group of atoms;

calculating a dipole moment induced in said at least one of said first group of atoms from said electric field using said anisotropic polarizability tensor;

calculating an interaction energy between said first group of atoms and said second group of atoms which includes a contribution from said induced dipole moment; and outputting said interaction energy.

19. The computer readable medium of claim 18, wherein said method additionally comprises retrieving, for said at least one of said first group of atoms, a permanent atomic quadrupole moment, a permanent atomic dipole moment, and an atomic charge.

20. The computer readable medium of claim 19, wherein said method additionally comprises calculating an interaction energy between said first group of atoms and said second group of atoms which includes a contribution from said permanent atomic quadrupole moment, permanent atomic dipole moment, and atomic charge.

21. An apparatus for modeling the geometry and energy of interaction between first and second groups of atoms comprising:

a data storage device storing an anisotropic atomic dipole polarizability tensor for at least one of said first group of atoms which was derived from elements of a quadrupole polarizability tensor of said first group of atoms;

a processor which (1) models an electric field produced at least in part by said first and second groups of atoms, (2) retrieves said anisotropic dipole polarizability tensor, (3) calculates a dipole moment induced in said at least one of said first group of atoms by said electric field, and (4) calculates an interaction energy between said first and second groups of atoms which includes a contribution from said induced dipole moment; and an output device which reports said calculated interaction energy or other physical property derived therefrom.

22. The method of claim 21, wherein said memory additionally stores a static atomic quadrupole moment, a static atomic dipole moment, and a charge for said at least one of said first group of atoms, and wherein said interaction energy includes a contribution from said static atomic quadrupole moment, said static atomic dipole moment, and said charge.

* * * * *